(12) United States Patent
Zhang

(10) Patent No.: US 9,650,400 B2
(45) Date of Patent: May 16, 2017

(54) VORICONAZOLE SODIUM PHOSPHATE HYDRATES AND POLYMORPHS THEREOF

(71) Applicant: SHAANXI SYNTHETIC PHARMACEUTICAL CO., LTD., Shaanxi (CN)

(72) Inventor: Qiyuan Zhang, Shaanxi Province (CN)

(73) Assignee: SHAANXI SYNTHETIC PHARMACEUTICAL Co., LTD., Shaanxi Province (CN)

( * ) Notice: Subject to any disclaimer, the term of this patent is extended or adjusted under 35 U.S.C. 154(b) by 0 days.

(21) Appl. No.: 14/917,133

(22) PCT Filed: Sep. 23, 2014

(86) PCT No.: PCT/CN2014/087195
§ 371 (c)(1),
(2) Date: Mar. 7, 2016

(87) PCT Pub. No.: WO2015/043453
PCT Pub. Date: Apr. 2, 2015

(65) Prior Publication Data
US 2016/0215008 A1    Jul. 28, 2016

(30) Foreign Application Priority Data
Sep. 28, 2013 (CN) .......................... 2013 1 0449024

(51) Int. Cl.
*C07F 9/6558* (2006.01)
(52) U.S. Cl.
CPC ............................. *C07F 9/65583* (2013.01)
(58) Field of Classification Search
CPC .................................................. C07F 9/65583
USPC .......................................... 544/243; 514/86
See application file for complete search history.

(56) References Cited

U.S. PATENT DOCUMENTS 6,790,957 B2 * 9/2004 Green ................ C07F 9/65181
544/243

FOREIGN PATENT DOCUMENTS

| CN | 101744778 A | 6/2010 |
|---|---|---|
| CN | 101824002 A | 9/2010 |
| CN | 103304600 A | 9/2012 |
| CN | 103524560 A | 1/2014 |

OTHER PUBLICATIONS

Adeyeye at el., Preformulation in Solid Dosage Form Development, Inform Healthcare, Chapter 2.3, 2008, pp. 63-80.*
Bastin et al., Salt Selection and Optimisation Procedures for Pharmaceutical New Chemical Entities, Organic Process Research & Development, 2000, 4, pp. 427-435.*
Gould et al., Salt Selection for Basic Drugs, International Journal of Pharmaceutics, 1986, 33, pp. 201-217.*
Liu et al., Water-Insoluble Drug Formulation, CRC Press, 2008, Chapter 15, pp. 417-435.*
Morris et al., An Integrated Approach to the Selection of Optimal Salt Form For a New Drug Candidate, International Journal of Pharmaceutics, 1994, 105, pp. 209-217.*
Serajuddin et al., Salt Formation to Improve Drug Solubility, Advanced Drug Delivery Reviews 59, 2007, pp. 603-616.*
Stahl et al., Handbook of Pharmaceutical Salts Proerties, Selection and Use, Wiley-VCH, 2008, pp. 265-327.*
Swarbrick et al., Salt Forms of Drugs and Absorption, Encyclopedia of Pharmaceuticals Technology 13, 1996, pp. 453-499.*
ISR for PCT/CN2014/087195, Dec. 29, 2014.

* cited by examiner

*Primary Examiner* — Deepak Rao
(74) *Attorney, Agent, or Firm* — AKC Patents, LLC; Aliki K. Collins

(57) ABSTRACT

The present invention relates to a voriconazole sodium phosphate hydrate, polymorphs thereof, a preparation method thereof, and use thereof, wherein the voriconazole phosphate salt hydrate prepared by using an isopropanol-water system, ethanol-water system, or an ethanol system comprises different crystal forms. And these kinds of crystal forms have favorable water solubility and stability and feature a simple manufacturing process. The voriconazole phosphate salt hydrate is principally used for treatment of fungal infections.

20 Claims, 6 Drawing Sheets

VORICONAZOLE SODIUM PHOSPHATE HYDRATES AND POLYMORPHS THEREOF

TECHNICAL FIELD

The present invention relates to a voriconazole sodium phosphate hydrate, polymorphs thereof, a preparation method thereof, and use thereof. Voriconazole sodium phosphate hydrate prepared as such and its polymorphs have better stability than its anhydrates.

TECHNICAL BACKGROUND

Voriconazole is a broad-spectrum triazole antifungal agent and it is indicated for treatment of invasive aspergillosis, serious invasive infections caused by fluconazole-resistant *Candida* (including *candida krusei*), and serious infections caused by *scedosporium* and *fusarium*. The pharmaceutical composition of the present invention mainly applies for treating progressive and life-threatening infections in immunodeficient patients. Voriconazole phosphate is a prodrug of the Voriconazole, which takes effects by being quickly hydrolyzed into voriconazole in body. Due to extremely poor water solubility of the voriconazole, a hydroxypropyl-β-cyclodextrin wrapping method is used in order to solubilize voriconazole for injection. However, this causes an increase in incidence rate of side effects. Hydroxypropyl-β-cyclodextrin is a novel excipient emerging in recent years. Since this excipient has a superior solubilizing effects on a plurality of poorly soluble drugs there is a trend that this excipient is rapidly increasingly used. However, its safety has not been deeply understood by now. It is reported in some literate that this excipient has somewhat hemolysis, renal toxicity and carcinogenicity, and may present more serious toxic side effects that remains unknown to us. Thus, care must be taken during its use. In foreign countries, there have been only few marketed drug preparations (e.g. drug products for treating serious infections or tumors) intended for particular indications in which hydroxypropyl-β-cyclodextrin is used, demonstrating the safety of the hydroxypropyl-β-cyclodextrin has not been sufficiently ascertained. Under such circumstance, in-depth study and observations shall be conducted on this excipient so as to further reveal its potential toxic and side effects instead of using it extensively in injections as a regular excipient. Adverse reactions caused by intravenous injection of hydroxypropyl-β-cyclodextrin mainly emerge as renal toxicity and hemolysis which are principally associated with known impurity of this excipient β-cyclodextrin. This impurity firstly induces vacuolar lesions at distal kidney tubules and produces giant lysosomes and noticeable acicular crystals in epidermal cells. It is speculated that the crystals are very likely to be a composite of cyclodextrin with cholesterols or lipoproteins. Later, significant changes take place in an organelle such as mitochondrial swelling, or irreversible breaking of intercellular tight junction between the Golgi apparatus and the cells at the fundus of smooth endoplasmic reticulum. Esterification of voriconazole phosphate is an effective measure to reduce these side effects. Voriconazole phosphate and its preparation methods have been disclosed in a plurality of Chinese patents.

BRIEF DESCRIPTION OF THE INVENTION

It is one objective of the present invention to provide a voriconazole sodium phosphate hydrate, its polymorphs, preparation method thereof, and a use thereof. The voriconazole sodium phosphate hydrate of the present invention features not only high absorbability, purity and stability but also its realization of industrialization.

It is the other objective of the present invention to provide a pharmaceutical composition containing the voriconazole sodium phosphate hydrate of the invention or its polymorphs, as well as use thereof.

The voriconazole sodium phosphate hydrate of the present invention has a structure as shown below.

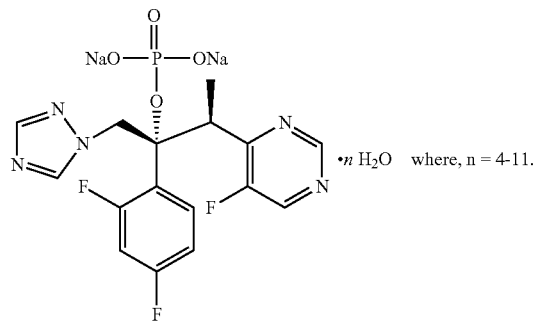

$\cdot n\,H_2O$ where, $n = 4\text{-}11$.

The method for preparing the voriconazole sodium phosphate of the invention comprises steps of:
1. Mixing voriconazole phosphate with an alkaline inorganic metal salt at an equimolar ratio of 1:1, adding an appropriate amount of water to react when heating, until the alkaline inorganic metal salt is dissolved completely, then stopping the heating.
2. After completion of step 1, adding low-polarity solvent slowly to mixture of the step 1 for precipitation, finally filtering the mixture to yield the voriconazole sodium phosphate hydrate;
   wherein in step 1, the reaction temperature is 0-80° C., and the alkaline metal salt is sodium bicarbonate, sodium carbonate, sodium hydroxide, or combination thereof, and the reaction solvent may be water or an aqueous polar solvents;
   and wherein in step 2, the low-polarity solvent is isopropanol, acetone, ethanol, or a mixture thereof.

The method for preparing the voriconazole sodium phosphate hydrate of the invention comprises following steps:
   adding voriconazole sodium phosphate into 1-55 volumes (W/V) aqueous solution of 50%-98% (V/V) low-polarity solvent, and stirring the resulting mixture at 0-80° C. until the solids are dissolved completely; adding 0-5% (W/V) activated carbon and stirring for 5 minutes; filtering the resulting mixture and allowing the filtrate to crystallize at room temperature for 24 hours; filtering out the solids and drying the resulting voriconazole sodium phosphate hydrate under reduced pressure at 5-60° C. for 24 hours;
   wherein the low-polarity solvent is acetone, acetonitrile, or isopropanol; and
   the voriconazole sodium phosphate hydrate obtained from the above steps has a water content of 10-35 wt %.

It is surprisingly found by the inventor of the present invention that the voriconazole sodium phosphate hydrate has different crystal forms under different refining and crystallization conditions, and three different crystal forms have been found by the inventor, and their X-ray powder diffraction patterns are shown in appended figures. Crystal form A was prepared by a method below.

Voriconazole sodium phosphate hydrate 10 g was added to 150 ml of 90% (V/V) isopropanol solution and stirred at 60° C. until the solids were dissolved. Filtration was followed and the resulting filtrate was allowed to stand still at room temperature for precipitation for 24 hours. Filtration was then performed and the filter cake was dried under vacuum at 40° C. for 24 hours to yield a crystal form A of the voriconazole sodium phosphate hydrate 5.2 g.

The measured data are shown below.

Water content: 25.32 wt %

The X-ray powder diffraction data is shown in FIG. 1.

Measured purity 99.97 wt % Area normalization method

The pattern is shown in FIG. 2

Crystal form B was prepared by the method below.

Voriconazole sodium phosphate hydrate 10 g was added to 20 ml of absolute ethanol and stirred at 60° C. until the solids were dissolved. Filtration was followed, and the resulting filtrate was allowed to stand still at room temperature for precipitation for 24 hours. Filtration was then performed and the filter cake was allowed to dry under vacuum at 40° C. for 24 hours, yielding the crystal form B of the voriconazole sodium phosphate hydrate 7.8 g.

The measured data are shown below.

Water content 25.35 wt %

The X-ray powder diffraction data are shown in FIG. 3.

The measured purity is 99.92 wt % Area normalization method

The pattern is shown in FIG. 4.

Crystal form C was prepared by the method below.

Voriconazole sodium phosphate hydrate 10 g was added to 20 ml of 90% (V/V) ethanol solution and stirred at 60° C. until the solids were dissolved. Filtration was followed, and the resulting filtrate was allowed to stand still at room temperature for precipitation for 24 hours. Filtration was then performed and the filter cake was allowed to dry under vacuum at 40° C. for 24 hours, yielding a crystal form C of the voriconazole sodium phosphate hydrate 6.4 g.

The measured data are shown below.

Water content 25.80 wt %

The X-ray powder diffraction data are shown in FIG. 5.

The measured purity 99.97 wt % Area normalization method

The pattern is shown in FIG. 6.

The voriconazole sodium phosphate hydrate and its polymorphs are useful, since they exhibit pharmacologic activity both in animals and in humans. In particular, this compound is useful in aspects of treatment or prevention of fungal infections. For example, it is suitable for treatment of topical fungal infections in human caused by *candida, trichophyton, sabouraudites, epidermophyton*, or for treatment of mucosal infections caused by *candida albicans*. The voriconazole sodium phosphate hydrate and its polymorphs may also be used for treatment of systemic fungal infections caused by *candida, cryptococcus neoformans, aspergillus flavus, aspergillus fumigatus, coccidioides, blastomyces brasiliensis, histoplasma,* or *blastomycetes*, and so forth.

A pharmaceutical composition containing the voriconazole sodium phosphate hydrate or its polymorphs of the present invention contains voriconazole sodium phosphate hydrate or its polymorphs in an amount of 25 mg-3000 mg per unit dosage (e.g. tablet, vial, or pouch), preferably 50 mg-1500 mg, and more preferably 50 mg-600 mg.

Pharmaceutical compositions comprising the voriconazole sodium phosphate hydrate or its polymorphs of the present invention may be administered in a form of unit dosage, and via an enteral or a parenteral route such as oral, intramuscular, or nasal routes, etc. Alternatively, the administration routes for the voriconazole sodium phosphate hydrate or its polymorphs of the present invention may be in an intravenous administration manner, and injection can comprise intravenous injection, subcutaneous injection, intramuscular injection, or acupoint injection, etc.

Pharmaceutical compositions comprising the voriconazole sodium phosphate hydrate or its polymorphs of the present invention may be administered in a dosage form such as tablets, capsules, dispersible tablets, oral liquids, infusion solutions, small needle preparations, lyophilized powder or any other pharmaceutically acceptable dosage forms. The method for preparing a lyophilized powder of voriconazole sodium phosphate hydrate or its polymorphs comprises steps of:

a. dissolving the voriconazole sodium phosphate hydrate or its polymorphs with water for injection, with or without addition of a stent agent or a stabilizer;
b. adjusting pH to a proper range using a pH regulator;
c. eliminating pyrogens from the resulting solution;
d. degerming the resulting solution;
e. filling the vials with the resulting solution; and
f. free-drying the resulting solution in the vials.

The stent agent may be selected from various pharmaceutically acceptable stent agents, which is preferably glucose, sodium chloride, lactose, hydrolyzed gelatin, mannitol, amino acids, or combinations thereof.

The pH regulator may be selected from the group consisting of organic acids, inorganic acids, inorganic bases, or organic bases, or any other pharmaceutically acceptable pH regulators.

The voriconazole sodium phosphate hydrate or its polymorphs of the present invention maintains their water solubility, as compared to its anhydrate. Furthermore, due to weak hydroscopicity, the voriconazole sodium phosphate hydrate or its polymorphs of the present invention exhibit unexpected improvements and handlability, which makes them suitable for use in oral or parenteral administrations.

Moreover, the voriconazole sodium phosphate hydrate or its polymorphs exhibit improved handlability as compared with the anhydrate, and thus are suitable for solid formulations.

Even further, the voriconazole sodium phosphate hydrate or its polymorphs of the present invention exhibit better solid state stability. As used herein, the term "solid state stability" refers to stability of an API under ambient and/or accelerated storage conditions. For example, voriconazole sodium phosphate hydrate or its polymorphs have weaker hydroscopicity, as compared to their anhydrates.

The compositions containing the voriconazole sodium phosphate hydrate or its polymorphs of the present invention are suitable for preparing anti-fungal drugs.

The details of one or more embodiments of the invention are set forth in the accompanying drawings and description below. Other features, objects and advantages of the invention will be apparent from the following description of the preferred embodiments, the drawings and from the claims.

BRIEF DESCRIPTION OF THE DRAWINGS

The present invention will he understood and appreciated more comprehensively from the following detailed description taken in conjunction with the appended drawings in which.

DETAILED DESCRIPTION OF THE INVENTION

Figure 1:
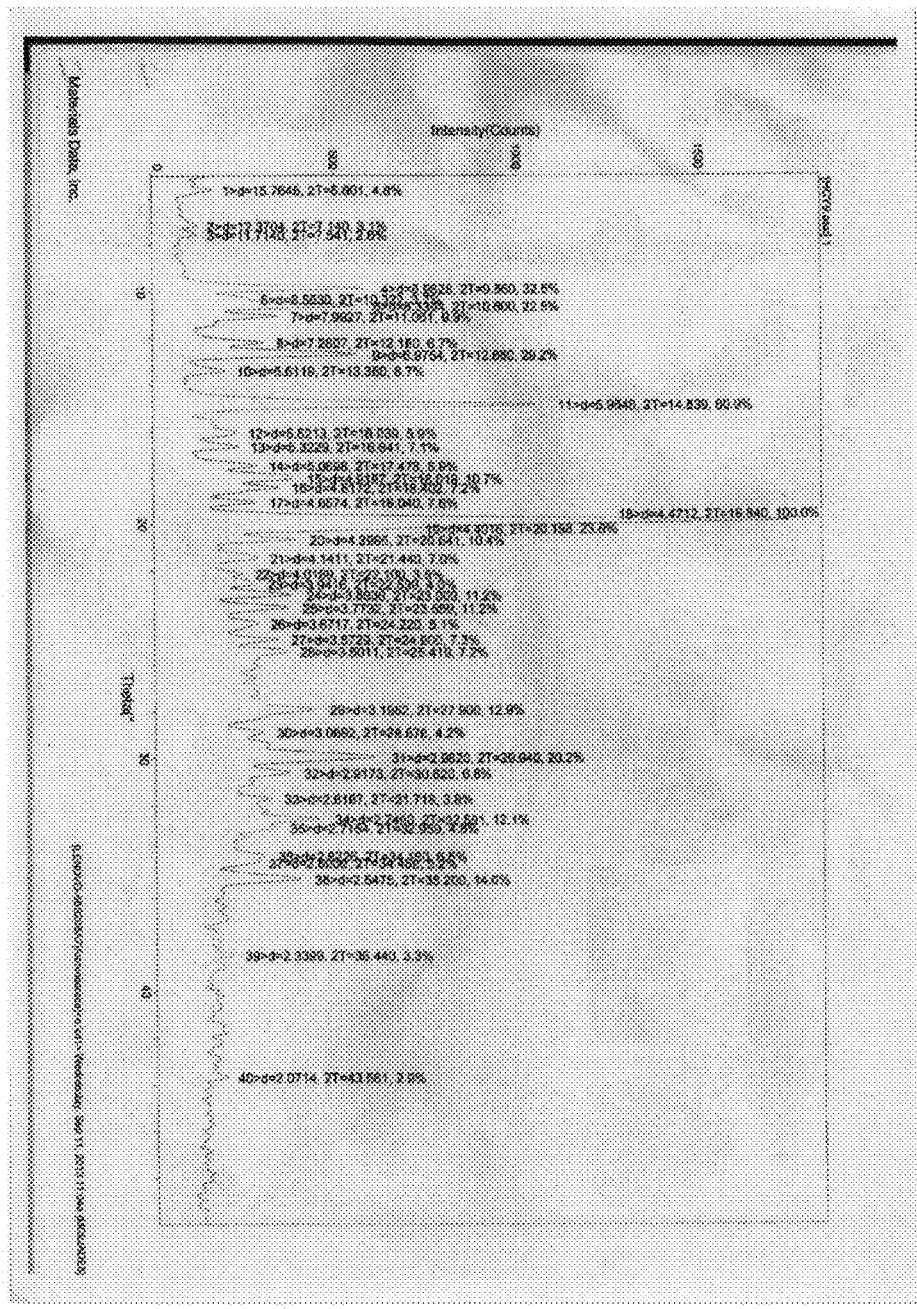
FIG. 1 is an XRD spectrum of crystal form A.
Figure 2:
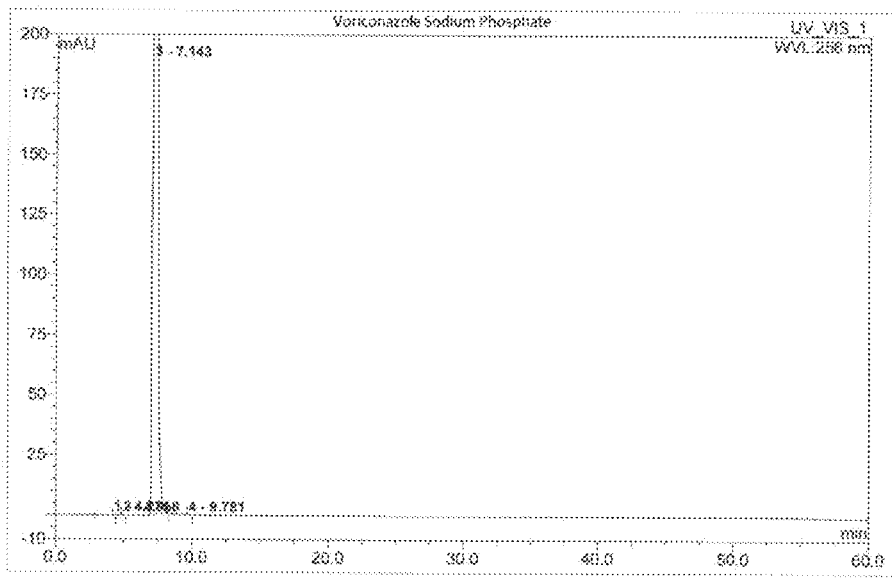
FIG. 2 is the spectrum for the determination of relative substances in crystal form A.
Figure 3:
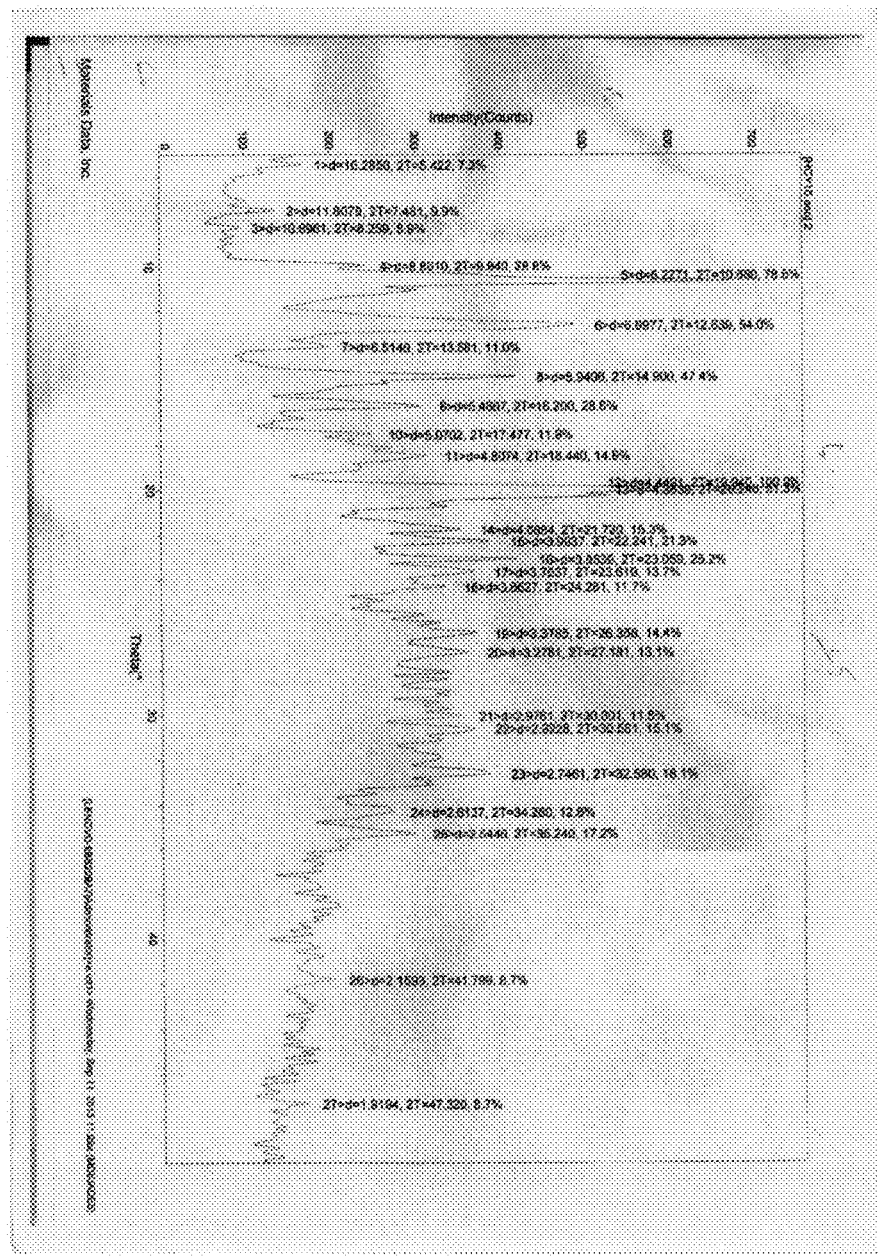
FIG. 3 is an XRD spectrum of crystal form B.
Figure 4:
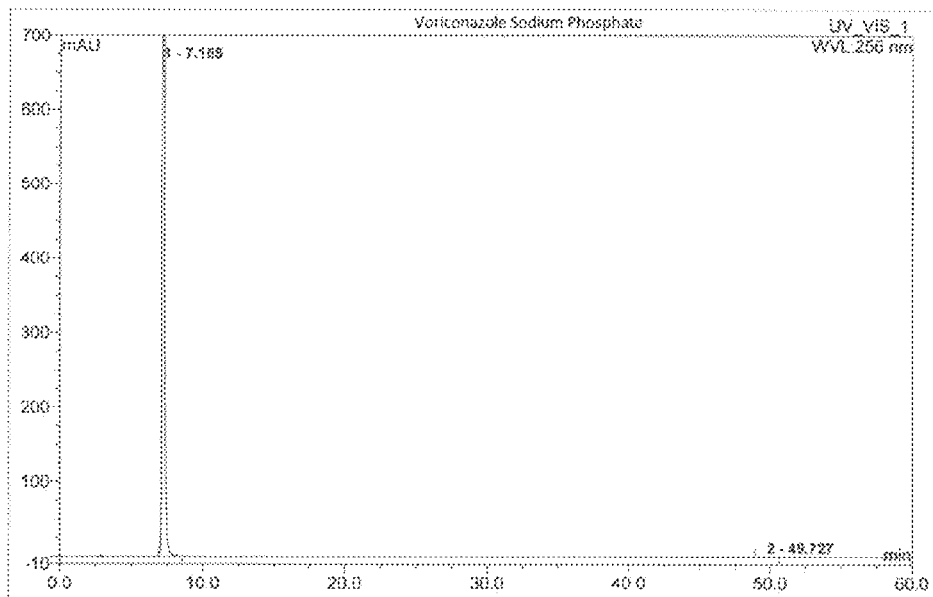
FIG. 4 is the spectrum for the determination of relative substances in crystal form B.
Figure 5:
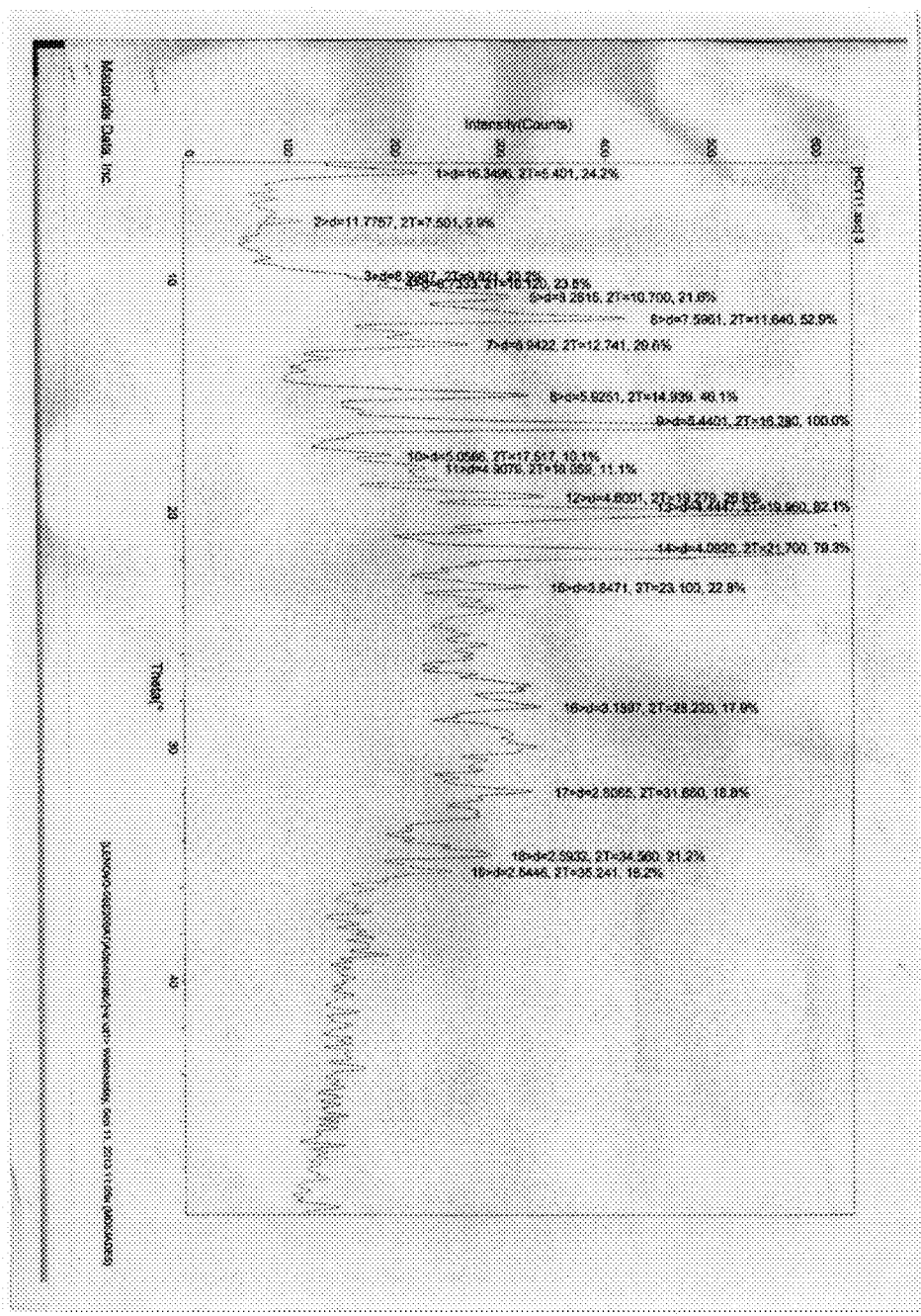
FIG. 5 is an XRD spectrum of crystal form C.
Figure 6:
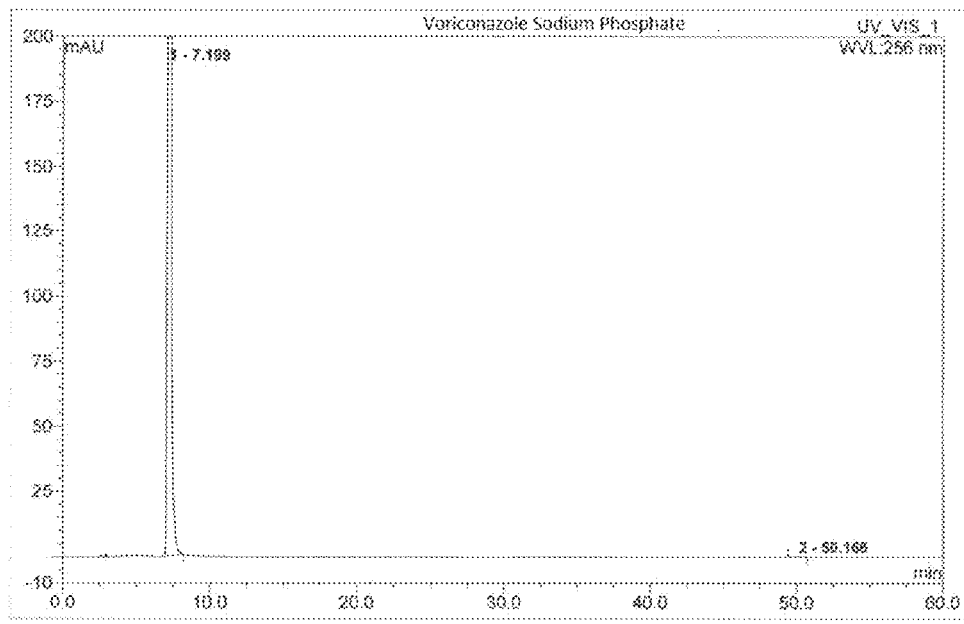
FIG. 6 is the spectrum for the determination of relative substances in crystal form C.

The present invention is now described in more detail in combination with the following examples. However, it should be understood that the scope of the present invention is not limited by these illustrative examples.

Example 1

Preparation of Voriconazole Sodium Phosphate Hydrate

Voriconazole sodium phosphate 100 g was dissolved using 15 volumes (W/V) of 90% (V/V) isopropanol water solution, and stirred under 60° C. until the solids were completely dissolved. And 0.5% (W/V) of activated carbon was added and the resulting mixture was stirred for 5 minutes. The mixture was filtered and the filtrate was allowed to crystallize at room temperature for 24 hours. And filtration was followed, yielding a voriconazole sodium phosphate hydrate, which was later dried under reduced pressure at 40° C. for 24 hours, and water content was measured as 25.7 wt %.

Example 2

Preparation of Voriconazole Sodium Phosphate Hydrate

Voriconazole sodium phosphate 10 g was dissolved using 55 volumes (W/V) of 90% (V/V) isopropanol water solution, and stirred under 60° C. until the solids were completely dissolved. And 0.5% (W/V) of activated carbon was added and the resulting mixture was stirred for 5 minutes. The mixture was filtered and the filtrate was allowed to crystallize at 5° C. for 24 hours. And filtration was followed, yielding a voriconazole sodium phosphate hydrate, which was dried under reduced pressure at 40° C. for 24 hours, and water content was measured as 25.3 wt %.

Example 3

Preparation of Voriconazole Sodium Phosphate Hydrate

Voriconazole sodium phosphate 10 g was dissolved using 8 volumes (W/V) of 70% (V/V) isopropanol water solution, and stirred under 60° C. until the solids were completely dissolved. And 0.5% (W/V) of activated carbon was added and the resulting mixture was stirred for 5 minutes. The mixture was filtered and the filtrate was allowed to crystallize at 15° C. for 24 hours. And filtration was followed, yielding a voriconazole sodium phosphate hydrate, which was dried under reduced pressure at 40° C. for 24 hours, and water content was measured as 27.5 wt %.

Example 4

Preparation of Voriconazole Sodium Phosphate Hydrate

Voriconazole sodium phosphate 10 g was dissolved using 2 volumes (W/V) of 70% (V/V) isopropanol water solution, and stirred under 60° C. until the solids were completely dissolved. And 0.5% (W/V) of activated carbon was added and the resulting mixture was stirred for 5 minutes. The mixture was filtered and the filtrate was allowed to crystallize at room temperature for 24 hours. And filtration was followed, yielding a voriconazole sodium phosphate hydrate, which was dried under reduced pressure at 50° C. to water content of 21.3 wt %.

Example 5

Preparation of Voriconazole Sodium Phosphate Hydrate

Voriconazole sodium phosphate 10 g was dissolved using 2 volumes (W/V) of 50% (V/V) isopropanol water solution, and stirred under 60° C. until the solids were completely dissolved. And 0.5% (W/V) of activated carbon was added and the resulting mixture was stirred for 5 minutes. The mixture was filtered and the filtrate was allowed to crystallize at 0° C. for 24 hours. And filtration was followed, yielding a voriconazole sodium phosphate hydrate, which was dried under reduced pressure at 40° C. for 24 hours, and water content was measured as 29.8 wt %.

Example 6

Preparation of Voriconazole Sodium Phosphate Hydrate

Voriconazole sodium phosphate 10 g was dissolved using 2 volumes (W/V) of 90% (V/V) ethanol water solution, and stirred under 60° C. until the solids were completely dissolved. And 0.5% (W/V) of activated carbon was added and the resulting mixture was stirred for 5 minutes. The mixture was filtered and the filtrate was allowed to crystallize at room temperature for 24 hours. And filtration was followed, yielding a voriconazole sodium phosphate hydrate, which was dried under reduced pressure at 40° C. for 24 hours, and water content was measured as 25.5 wt %.

Example 7

Preparation of Voriconazole Sodium Phosphate Hydrate

Voriconazole sodium phosphate 10 g was dissolved using 10 volumes (W/V) of 90% (V/V) ethanol water solution, and stirred under 60° C. until the solids were completely dissolved. And 0.5% (W/V) of activated carbon was added and the resulting mixture was stirred for 5 minutes. The mixture was filtered and the filtrate was allowed to crystallize at 5° C. for 24 hours. And filtration was followed, yielding a voriconazole sodium phosphate hydrate, which was dried under reduced pressure at room temperature for 24 hours, and water content was measured as 30.0 wt %.

Example 8

Preparation of Voriconazole Sodium Phosphate Hydrate

Voriconazole sodium phosphate 10 g was dissolved using 5 volumes (W/V) of 60% (V/V) ethanol water solution, and stirred under 60° C. until the solids were completely dissolved. And 0.5% (W/V) of activated carbon was added and the resulting mixture was stirred for 5 minutes. The mixture was filtered and the filtrate was allowed to crystallize at 0° C. for 24 hours. And filtration was followed, yielding a voriconazole sodium phosphate hydrate, which was dried under reduced pressure at 40° C. to water content of 24.8 wt %.

Example 9

Preparation of Voriconazole Sodium Phosphate Hydrate

Voriconazole sodium phosphate 10 g was dissolved using 2 volumes (W/V) of ethanol solution, and stirred under 60° C. until the solids were completely dissolved. And 0.5% (W/V) of activated carbon was added and the resulting mixture was stirred for 5 minutes. The mixture was filtered and the filtrate was allowed to crystallize at room temperature for 24 hours. And filtration was followed, yielding a voriconazole sodium phosphate hydrate, which was dried under reduced pressure at 50° C. to water content of 18.4 wt % (purity 98.2 wt %).

Example 10

Preparation of Voriconazole Sodium Phosphate Hydrate

Voriconazole sodium phosphate 10 g was dissolved using 2 volumes (W/V) of ethanol solution, and stirred under 40° C. until the solids were completely dissolved. And 0.5% (W/V) of activated carbon was added and the resulting mixture was stirred for 5 minutes. The mixture was filtered and the filtrate was allowed to crystallize at room temperature for 24 hours. And filtration was followed, yielding a voriconazole sodium phosphate hydrate, which was dried under reduced pressure at 60° C. to water content of 13.5 wt % (purity 97.8 wt %).

Example 11

Preparation of Voriconazole Sodium Phosphate Hydrate

Voriconazole sodium phosphate 10 g was dissolved using 10 volumes (W/V) of 90% (V/V) water solution of acetone, and stirred under 40° C. until the solids were completely dissolved. And 0.5% (W/V) of activated carbon was added and the resulting mixture was stirred for 5 minutes. The mixture was filtered and the filtrate was allowed to crystallize at room temperature for 24 hours. And filtration was followed, yielding a voriconazole sodium phosphate hydrate, which was dried under reduced pressure at 50° C. to water content of 19.8 wt % (purity 98.9 wt %).

Example 12

Preparation of Voriconazole Sodium Phosphate Hydrate

Voriconazole sodium phosphate 10 g was dissolved using 6 volumes (W/V) of 90% (V/V) acetone water solution, and stirred under 40° C. until the solids were completely dissolved. And 0.5% (W/V) of activated carbon was added and the resulting mixture was stirred for 5 minutes. The mixture was filtered and the filtrate was allowed to crystallize at room temperature for 24 hours. And filtration was followed, yielding a voriconazole sodium phosphate hydrate, which was dried under reduced pressure at 60° C. to water content of 15.9 wt % (purity 97.9 wt %).

Example 13

Preparation of Voriconazole Sodium Phosphate Hydrate

Voriconazole sodium phosphate 10 g was dissolved using 15 volumes (W/V) of 90% (V/V) acetone water solution, and stirred under 40° C. until the solids were completely dissolved. And 0.5% (W/V) of activated carbon was added and the resulting mixture was stirred for 5 minutes. The mixture was filtered and the filtrate was allowed to crystallize at room temperature for 24 hours. And filtration was followed, yielding a voriconazole sodium phosphate hydrate, which was dried under reduced pressure at 40° C. to a water content of 23.5 wt % (Purity 99.1 wt %).

Example 14

Preparation of Voriconazole Sodium Phosphate Crystal Form A

Voriconazole sodium phosphate hydrate 10 g of example 1 was dissolved using 15 volumes (W/V) of 90% (V/V) isopropanol water solution, and stirred under 60° C. until the solids were completely dissolved. And 0.5% (W/V) of activated carbon was added and the resulting mixture was stirred for 5 minutes. The mixture was filtered and the filtrate was allowed to crystallize at room temperature for 24 hours. And filtration was followed, yielding a voriconazole sodium phosphate hydrate, which was dried under reduced pressure at 40° C. for 24 hours, and water content was measured as 25.32 wt %. The results for the crystal form are shown as the results in table below for X-ray powder diffraction.

TABLE 1

Results for X-ray Powder Diffraction of Crystal Form A

| No. | d | 2T | Percent |
|---|---|---|---|
| 1 | 8.9628 | 9.860 | 32.5 |
| 2 | 8.3394 | 10.600 | 22.5 |
| 3 | 6.9754 | 12.680 | 29.2 |
| 4 | 5.9648 | 14.839 | 60.9 |
| 5 | 4.4712 | 19.840 | 100.0 |
| 6 | 4.4016 | 20.158 | 23.6 |
| 7 | 2.9820 | 29.940 | 20.2 |

Example 15

Preparation of Voriconazole Sodium Phosphate Crystal Form B

Voriconazole sodium phosphate hydrate 10 g of example 1 was dissolved using 2 volumes (W/V) of absolute ethanol solution, and stirred under 60° C. until the solids were completely dissolved. And 0.5% (W/V) of activated carbon was added and the resulting mixture was stirred for 5 minutes. The mixture was filtered and the filtrate was allowed to crystallize at room temperature for 24 hours. And filtration was followed, yielding a voriconazole sodium phosphate hydrate, which was dried under reduced pressure at 40° C. for 24 hours, and water content was measured as 25.35 wt %. The results for this crystal form are shown as the Results for X-ray powder diffraction in table below.

TABLE 2

Results for X-ray Powder Diffraction of Crystal Form B

| No. | d | 2T | Percent |
|---|---|---|---|
| 1 | 8.8910 | 9.9400 | 28.8 |
| 2 | 8.2771 | 10.6800 | 78.5 |
| 3 | 6.9977 | 12.6390 | 54.0 |
| 4 | 5.9406 | 14.9000 | 47.4 |
| 5 | 5.4667 | 16.2000 | 28.6 |
| 6 | 4.4491 | 19.9400 | 100.0 |
| 7 | 4.3839 | 20.2400 | 51.3 |
| 8 | 3.9937 | 22.2410 | 21.3 |
| 9 | 3.8539 | 23.0590 | 25.2 |

Example 16

Preparation of Voriconazole Sodium Phosphate Crystal Form C

Voriconazole sodium phosphate hydrate 10 g of example 1 was dissolved using 2 volumes (W/V) of 90% (V/V) ethanol solution, and stirred under 60° C. until the solids were completely dissolved. And 0.5% (W/V) of activated carbon was added and the resulting mixture was stirred for 5 minutes. The mixture was filtered and the filtrate was allowed to crystallize at room temperature for 24 hours. And filtration was followed, yielding a voriconazole sodium phosphate hydrate, which was dried under reduced pressure at 40° C. for 24 hours, and water content was measured as 25.80 wt %. The results for this crystal form are shown as the results for X-ray powder diffraction in the table below.

TABLE 3

Results for X-Ray Powder Diffraction of Crystal Form C

| No. | d | 2T | Percent |
|---|---|---|---|
| 1 | 16.3496 | 5.4010 | 24.2 |
| 2 | 8.9987 | 9.8210 | 20.2 |
| 3 | 8.7333 | 10.1200 | 23.8 |
| 4 | 8.2615 | 10.7000 | 21.6 |
| 5 | 7.5961 | 11.6400 | 52.9 |
| 6 | 6.9422 | 12.7410 | 29.6 |
| 7 | 5.9251 | 14.9390 | 46.1 |
| 8 | 5.4401 | 16.2800 | 100.0 |
| 9 | 4.6001 | 19.2790 | 26.8 |
| 10 | 4.4447 | 19.9600 | 82.1 |
| 11 | 4.9200 | 21.7000 | 79.3 |
| 12 | 3.8471 | 23.1000 | 22.8 |
| 13 | 3.1597 | 28.2200 | 17.9 |
| 14 | 2.8065 | 31.8600 | 18.8 |
| 15 | 2.5932 | 34.5600 | 21.2 |

Example 17

Preparation of Voriconazole Sodium Phosphate Hydrate Freeze-Dry Agent

Voriconazole sodium phosphate hydrate 135.5 g (calculated as voriconazole sodium phosphate) with or without addition of an appropriate amount of pharmaceutical excipient, was added to 800 ml of water for injection and dissolved at room temperature. The pH of the resulting solution was adjusted to 6-11 using a pH regulator. Then 200 ml of water for injection was added, followed by addition 0.1% (W/V) of activated carbon for 10 minutes' decoloration. And the solution was filtered using a 0.22 μm millipore membrane The filtrate was filled into the vials, 1 ml filtrate solution for each vial, the vials were loosely capped and freezed at −60° C. for 4 hours. Then the freezing temperature was slowly increased to −20° C., meanwhile a vacuum pump was activated for 18 hours' evacuation. Temperature of a partition board was raised to 0° C. and dried under vacuum for 6 hours, and the temperature was further raised to 15° C. and dried under vacuum for 4 hours. The vials were pressed and capped completely.

Example 18

Preparation of Voriconazole Sodium Phosphate Hydrate Enteric-Coated

| Tablet | |
|---|---|
| Tablet core formulation | Weight of Sample |
| Preparation of voriconazole sodium phosphate hydrate | 135.5 g |
| Lactose | 800 g |
| Sodium carbonate | 5 g |
| Magnesium stearate | 0.7 g |
| | Production 1,000 tablets |
| Isolation layer formulation | |
| OPADRY 295K690000 | 6.0% (W/V) solution |
| 85% (V/V) ethanol | |
| Weight increase for isolation layer about 3-5%% | |
| Enteric coating layer formulation | |
| ACRYL-EZE 93018509 | 20.0% (W/V) solution |
| Water | |

Weight increase of enteric coating layer was about 7-12 wt % a. voriconazole sodium phosphate and sodium carbonated were weighed respectively and passed through a 100-mesh sieve for further use;

b. a lactose was weighed and passed through a 20-mesh sieve for further use and magnesium stearate was passed through a 100-mesh sieve for further use;

c. the voriconazole sodium phosphate, the lactose, the sodium carbonate, and magnesium stearate were uniformly mixed in accordance with the amount in formulation;

d. content of an intermediate was measured and a tablet weight was determined, then the mixture was subject to tableting;

e. the resulting plain tablets were coated with the isolation layer (weight increase of the isolation layer was 3-5 wt %);

f. the resulting plain tablets were coated with a enteric coating layer (weight increase of the isolation layer was 7-12 wt %).

Example 19

Hydroscopicity Comparison Between Voriconazole Phosphate Anhydrate and Voriconazole Phosphate Hydrate Voriconazole phosphate anhydrate and Voriconazole phosphate hydrate were prepared using different methods, and placed under conditions of 25° C. and 80% humidity for 24 hours, and then the weight increase due to moisture absorption was determined. The results are shown in table 4.

TABLE 4

Results for Moisture Absorption between Voriconazole Phosphate Anhydrate and Voriconazole Phosphate Hydrate

| Sample | Time | | Weight increase by moisture absorption, by weight |
|---|---|---|---|
| | 0 hour | 24 hours | |
| Voriconazole Phosphate Hydrate | 0.3318 g | 0.3441 g | 3.6% |
| Voriconazole Phosphate Anhydrate | 0.3938 g | 0.4627 g | 17.5% |

The results show that the voriconazole phosphate anhydrate exhibits significant hydroscopicity, while the Voriconazole phosphate hydrate exhibits mild hydroscopicity and does not nictitate stringent storage conditions.

Example 20

Comparison of Related Substances after Moisture Absorption for Voriconazole Phosphate Anhydrate Versus Voriconazole Phosphate Hydrate Sample injection was carried out by using a sample prepared by allowing the sample in Example 17 to absorb moisture, and the results are shown in Table 5.

TABLE 5

Results for Related Substances after Moisture Absorption For Voriconazole Phosphate Anhydrate Versus Voriconazole Phosphate Hydrate

| Sample | Time | |
|---|---|---|
| | 0 hour (impurity, by weight) | 24 hour (impurity, by weight) |
| Voriconazole phosphate hydrate | Individual impurity 0.06% Total impurity 0.09% | Individual impurity 0.08% Total impurity 0.13% |
| Voriconazole phosphate anhydrate | Individual impurity 0.07% Total impurity 0.10% | Individual impurity 0.30% Total impurity 0.37% |

The results show that, there was minor change in impurity for voriconazole phosphate hydrate after absorbing the moisture for 24 hours, while there was more than one time of increase in impurities of voriconazole phosphate anhydrate, which was extremely unstable under highly humid conditions and required very stringent storage conditions. Therefore, the voriconazole phosphate hydrate had advantages over the Voriconazole phosphate.

Example 21

Pharmacokinetic Experiments

Two rabbits of same body weight were intravenously administered equimolar voriconazole sodium phosphate and voriconazole, respectively, and an equal volume of blood was drawn from the rabbits at different time intervals, and a metabolism status in body was determined. The results were shown in Table 6.

TABLE 6

Results for Pharmacokinetic Experiments

| | | 30 min | 60 min | 120 min | 150 min | 200 min | 250 min |
|---|---|---|---|---|---|---|---|
| Administration of voriconazole sodium phosphate | Prodrug | 235.92 | 143.51 | 98.59 | 2.045 | 0 | 0 |
| | parent nucleus | 0.324 | 86.42 | 158.32 | 186 37 | 130.38 | 69.23 |
| Administration of voriconazole | | 378.34 | 321.69 | 150.45 | 78.35 | 29.71 | 0.234 |

Note:
The above data are all peak areas.

The results show that voriconazole sodium phosphate can be metabolized into voriconazole in body to produce its pharmacodynamic effects.

Example 22

Pharmacological and Pharmacodynamic Experiments

1. Diffused Aspergillosis and Candidiasis in Guinea Pigs

In all experiments, particular pathogen-free guinea pigs (body weight of 400-500 g) were used. A conduit was placed in the left jugular vein of the attached to the animal was infected with *Aspergillus fumigatus* (4,000 CFU/g body weight) or *Candida albicans* (4,000 CFU/g body weight) via the lateral veins of penis of the animal or via the implanted conduit. One hour after infection, the animals were subject to an intravenous therapy (5 mg/kg/day). The mean survival time (MST) and the percent survival (% sur) were recorded for each group experimental animals (the number of each group of experimental animals is listed in column "N") within respective number of days. The amounts of *candida albicans* and *candida albicans* in deep tissues (such as liver, spleen, kidney, lung, or brain) were investigated in animals which died during the experiment and in animals which survived the experiment but were later sacrificed in respective groups. The colony forming units per gram (CFU/g) was measured in the culture-positive liver and is listed in Table 3. The results are shown in Table 3 as mean log 10 CFU/g. "% neg" in Table 1 represents the percent of deep tissues that were culture-negative after treatment. Thus, the relatively potent test compound exhibits higher values in columns "MST", "% sur" and "% neg", but exhibits a low value in column "CFU/g".

TABLE 7

Results for Pharmacology and Pharmacodynamics

| Compound | N | MST (days) | % sur | g (liver) | % neg | N | MST (days) | % sur | g (liver) | % neg |
| --- | --- | --- | --- | --- | --- | --- | --- | --- | --- | --- |
| Placebo | 6 | 5.1 | 0 | 4.8 | 6 | 10 | 2.7 | 0 | 4.8 | 3 |
| voriconazole sodium phosphate hydrate | 6 | 6.2 | 66.4 | 3.5 | 70 | 10 | 9.5 | 76.9 | 0 | 69 |

It is seen from the above data that voriconazole sodium phosphate is very potent against fungal infection.

The invention claimed is:

1. A voriconazole sodium phosphate hydrate, the sodium voriconazole phosphate hydrate has a chemical structure as shown below:

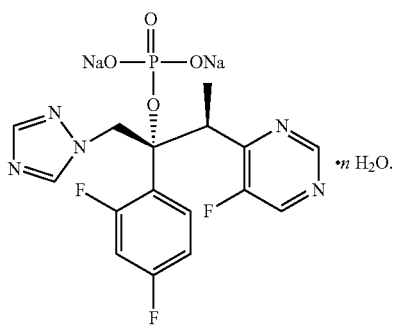

n = 4-11

2. The voriconazole sodium phosphate hydrate of claim 1, comprising crystal form A of voriconazole sodium phosphate hydrate, wherein 2θ value of X-ray powder diffraction pattern is about: 9.860, 10.600, 12.680, 14.839, 19.840, 20.148, or 29.940.

3. The voriconazole sodium phosphate hydrate of claim 1, comprising crystal form B of voriconazole sodium phosphate hydrate, wherein 2θ value of X-ray powder diffraction pattern is about: 10.680, 12.639, 14.900, 19.940, 20.240, or 23.059.

4. The voriconazole sodium phosphate hydrate of claim 1, comprising crystal form C of voriconazole sodium phosphate hydrate, wherein 2θ value of X-ray powder diffraction pattern is about: 11.640, 12.741, 14.939, 16.280, 19.960, or 21.700.

5. A pharmaceutical composition, wherein active ingredient of the composition is the voriconazole sodium phosphate hydrate of claim 1 in an amount of 0.01-99.99% by weight.

6. The composition in claim 5, wherein the composition is a parenterally administered preparation.

7. The composition of claim 5, wherein the composition is an orally administered preparation.

8. The composition of claim 6, wherein the parenterally administered preparation is an injection or, powder for injection.

9. The composition of claim 7, wherein the orally administered preparation is a tablet, a dispersible tablet, a capsule, a granule, or an oral liquid.

10. The composition of claim 5, wherein the composition preparation contains 50-3000 mg of voriconazole sodium phosphate hydrate in each tablet, vial, pouch, or piece.

11. The pharmaceutical composition of claim 5 administered as an anti-fungal drug for treating fungal infections.

12. A method for preparing voriconazole sodium phosphate hydrate or its polymorphs, comprising steps of:
adding 1-20 L/Kg of alcohol-water system or ketone-water system to a container containing voriconazole sodium phosphate;
heating the resulting mixture to 40° C.-70° C. under stirring;
stirring the mixture for 5-30 minutes under incubation;
filtering the mixture when it is still hot and cooling the filtrate to room temperature;
allowing the filtrate to crystallized at 0° C.-15° C. for 1-48 hours;
filtering out resulting solids and washing the solids with acetone; and
drying the solids at 30° C.-75° C. to an approximate theoretical water content until formation of the voriconazole sodium phosphate hydrate of claim 1.

13. A method for preparing polymorphs of the voriconazole sodium phosphate hydrate of claim 12, wherein solution used to prepare crystal form A of the voriconazole sodium phosphate hydrate is a 90% (V/V) isopropanol-water system; solution used to prepare crystal form B of the voriconazole sodium phosphate hydrate is a ethanol-water system, and solution used prepare crystal form C of the voriconazole sodium phosphate hydrate is a 90% (V/V) ethanol-water system.

14. The method for preparing the voriconazole sodium phosphate hydrate of claim 12, wherein the alcohol-water system is ethanol-water system, isopropanol-water system, and the ketone-water system is acetone-water.

15. A pharmaceutical composition, wherein active ingredient of the composition is the voriconazole sodium phosphate hydrate of claim 2 in an amount of 0.01-99.99% by weight.

16. The composition of claim 15, wherein the composition preparation contains 50-3000 mg of voriconazole sodium phosphate hydrate in each tablet, vial, pouch, or piece.

17. A pharmaceutical composition, wherein active ingredient of the composition is the voriconazole sodium phosphate hydrate of claim 3 in an amount of 0.01-99.99% by weight.

18. The composition of claim 17, wherein the composition preparation contains 50-3000 mg of voriconazole sodium phosphate hydrate in each tablet, vial, pouch, or piece.

19. A pharmaceutical composition, wherein active ingredient of the composition is the voriconazole sodium phosphate hydrate of claim 4 in an amount of 0.01-99.99% by weight.

20. The composition of claim 19, wherein the composition preparation contains 50-3000 mg of voriconazole sodium phosphate hydrate in each tablet, vial, pouch, or piece.

* * * * *